(12) United States Patent
Chiriac et al.

(10) Patent No.: US 11,344,247 B2
(45) Date of Patent: May 31, 2022

(54) APPARATUS FOR DETERMINING ABNORMAL ELECTRIC POTENTIALS IN VENTRICULAR MYOCARDIUM

(71) Applicant: INSTITUTUL NATIONAL DE CERCETARE-DEZVOLTARE PENTRU FIZICA TEHNICA—IFT IASI, Iasi (RO)

(72) Inventors: Horia Chiriac, Iasi (RO); Mihaela Grecu, Iasi (RO); Sorin Corodeanu, Iasi (RO); Mihai Tibu, Iasi (RO); Nicoleta Lupu, Iasi (RO)

(73) Assignee: INSTITUTUL NATIONAL DE CERCETARE-DEZVOLTARE PENTRU FIZICA TEHNICA—IFT IASI, Iasi (RO)

( * ) Notice: Subject to any disclaimer, the term of this patent is extended or adjusted under 35 U.S.C. 154(b) by 0 days.

(21) Appl. No.: 16/308,191

(22) PCT Filed: Jun. 6, 2017

(86) PCT No.: PCT/RO2017/000010
§ 371 (c)(1),
(2) Date: Dec. 7, 2018

(87) PCT Pub. No.: WO2017/213533
PCT Pub. Date: Dec. 14, 2017

(65) Prior Publication Data
US 2019/0183375 A1  Jun. 20, 2019

(30) Foreign Application Priority Data

Jun. 7, 2016 (RO) .............................. a 2016 00415

(51) Int. Cl.
*A61B 5/366* (2021.01)
*A61B 5/00* (2006.01)
(Continued)

(52) U.S. Cl.
CPC .............. *A61B 5/366* (2021.01); *A61B 5/287* (2021.01); *A61B 5/363* (2021.01); *A61B 5/4848* (2013.01);
(Continued)

(58) Field of Classification Search
CPC ... A61B 5/0472; A61B 5/0422; A61B 5/0464; A61B 5/4848
See application file for complete search history.

(56) References Cited

U.S. PATENT DOCUMENTS 5,046,504 A  9/1991 Albert et al.
2012/0101397 A1  4/2012 Blomqvist
(Continued)

FOREIGN PATENT DOCUMENTS

WO  WO 2010/151181 A1  12/2010
WO  WO 2012/139116 A2  10/2012

OTHER PUBLICATIONS

International Search Report in International Application No. PCT/RO2017/000010, dated Nov. 8, 2017.
(Continued)

*Primary Examiner* — Joseph M Dietrich
(74) *Attorney, Agent, or Firm* — Hershkovitz & Associates, PLLC; Abe Hershkovitz (57) ABSTRACT

The invention refers to an apparatus that determines the abnormal electrical potential points which appear in the ventricular myocardium, particularly the left ventricle, which are capable of generating arrhythmias with a serious impact. The apparatus may assist the physician in objectively identifying, in real time, of the points which require ablating. The apparatus to determine the points of abnormal electrical potential from the ventricular myocardium contains an amplification and analogue filtering module, an analogue to digital signal converter, a hardware device
(Continued)

which contains a microchip for digital processing, by means of a software, of signals received from an EKG and a catheter, with a display for the visualization of the signals received from the EKG and the catheter, as well as the abnormal electrical potentials found in the ventricular myocardium, identified via the software. The software analyzes the received signal from the catheter, referring to the amplitude, duration and synchronization with the QRS complex of the signal received from the EKG, as well as the degree of spectral fragmentation.

18 Claims, 8 Drawing Sheets

(51) Int. Cl.
    *A61B 5/287*     (2021.01)
    *A61B 5/363*     (2021.01)
    *A61B 5/316*     (2021.01)

(52) U.S. Cl.
    CPC .......... *A61B 5/6852* (2013.01); *A61B 5/7257* (2013.01); *A61B 5/743* (2013.01); *A61B 5/7415* (2013.01); *A61B 5/316* (2021.01); *A61B 5/7264* (2013.01); *A61B 2505/05* (2013.01)

(56) References Cited

U.S. PATENT DOCUMENTS

| | | | |
|---|---|---|---|
| 2014/0023256 | A1 | 1/2014 | Nazarian et al. |
| 2014/0200429 | A1 | 7/2014 | Spector et al. |
| 2014/0200430 | A1 | 7/2014 | Spector et al. |
| 2014/0200471 | A1 | 7/2014 | Spector et al. |
| 2014/0200571 | A1 | 7/2014 | Spector et al. |
| 2014/0200572 | A1 | 7/2014 | Spector et al. |
| 2014/0200575 | A1 | 7/2014 | Spector et al. |
| 2015/0032171 | A1 | 1/2015 | Ghosh |

OTHER PUBLICATIONS

Bethge C. et al., "Hypertensive heart disease and endocardially recorded late potentials," Journal of Cardiovascular Pharmacology, Raven Press, New York, NY, vol. 10, No. 6, Jan. 1, 1987, pp. S129-S134, XP003027046, ISSN: 0160-2446.

Bogun F et al., "Relationship of frequent postinfarction premature ventricular complexes to the reentry circuit of scar-related ventricular tachycardia," Heart Rhythm, Elsevier, US, vol. 5. No. 3, Mar. 1, 2008, pp. 367-374, XP025408517, ISSN: 1547-5271, DOI: 10.1016/J.HRTHM.2007.11.026.

Raymond J.-M., Sacher F., Winslow R., Tedrow U., et al., "Catheter ablation for scar-related ventricular tachycardias," Curr Probl Cardiol, 2009, 34, pp. 225-270.

De Bakker J.M., van Capelle F.J., Janse M.J., et al., "Reentry as a cause of ventricular tachycardia in patients with chronic ischemic heart disease: Electrophysiologic and anatomic correlation," Circulation, 1988, 77, pp. 589-606.

Haqqani H.M., Marchlinski F.E., "Electrophysiologic substrate underlying postinfarction ventricular tachycardia: characterization and role in catheter ablation," Heart Rhythm, 2009, 6, pp. S70-S76.

Desjardins B., Crawford T., Good E., et al., "Infarct architecture and characteristics on delayed enhanced magnetic resonance imaging and electroanatomic mapping in patients with postinfarction ventricular arrhythmia," Heart Rhythm, 2009, 6(5) pp. 644-651.

Wissner E., Stevenson W.G., Kuck K.H., "Catheter ablation of ventricular tachycardia in ischaemic and non-ischaemic cardiomyopathy: where are we today? A clinical review," European Heart Journal, 2012, 33, pp. 1440-1450.

Stevenson W.G., Khan H., Sager P., et al., "Identification of reentry circuit sites during catheter mapping and radiofrequency ablation of ventricular tachycardia late after myocardial infarction," Circulation, 1993, 88, pp. 1647-1670.

Arenal A., del Castillo S., Gonzalez-Torrecilla E., et al., "Tachycardia-related channel in the scar tissue in patients with sustained monomorphic ventricular tachycardias: Influence of the voltage scar definition," Circulation. 2004, 110, pp. 2568-2574.

Aliot E.M., Stevenson W.G., Almendral-Garrote J.M., et al., "EHRA/HRS expert consensus on catheter ablation of ventricular arrhythmias," Heart Rhythm, Europace, 2009, 11, pp. 771-817.

Wijnmaalen A.P., van der Geest R.J., van Huls van Taxis C.F., et al., "Head-to-head comparison of contrast-enhanced magnetic resonance imaging and electroanatomical voltage mapping to assess post-infarct scar characteristics in patients with ventricular tachycardias: real-time image integration and reversed registration," Eur Heart J, 2011, 32, pp. 104-114.

Vergara P., Trevisi N., Ricco A., et al., "Late potentials abolition as an additional technique for reduction of arrhythmia recurrence in scar related ventricular tachycardia ablation," J Cardiovasc Electrophysiol, 2012, pp. 1-7.

Berruezo A., Fernández-Armenta J., Andreu D., et al., "Scar Dechanneling: A New Method for Scar-Related Left Ventricular Tachycardia Substrate Ablation," Circ Arrhythm Electrophysiol, published online Jan. 12, 2015; DOI: 10.1161/CIRCEP.114.002386.

Fernández-Armenta J., Berruezo A., Ortiz-Perez J.T., et al., "Improving Safety of Epicardial Ventricular Tachycardia Ablation Using the Scar Dechanneling Technique and the Integration of Anatomy, Scar Components, and Coronary Arteries Into the Navigation System," Circulation, 2012, 125, pp. e466-e468.

APPARATUS FOR DETERMINING ABNORMAL ELECTRIC POTENTIALS IN VENTRICULAR MYOCARDIUM

INTRODUCTION

Medical systems used in the medical field in general and especially in cardiology provide complex electrical signals which are in many situations difficult to interpret. A particular case is represented by the monitoring systems used during ablation interventions, in which the decision regarding the area where the cauterization will be performed is based on the surface real-time electrocardiogram signals and the electrical signal recorded from the electrodes used with the catheter in the analyzed zone, respectively the intracardiac area. The physician makes this estimation based on certain recorded signals characteristics and decides if the respective area must be cauterized or not, keeping track of more instruments simultaneously.

TECHNICAL FIELD

The present invention relates to an apparatus for determining the abnormal electrical potential points which occur in ventricular myocardial tissue, especially in the left ventricle, being able to generate heart rhythm disorders with vital impact.

The invention allows a much more exact localization of those points with risk for tachycardia/ventricular arrhythmia, which require ablation. Thus, viable zones in the ventricular mass surviving after a myocardial infarction are recovered/saved.

BACKGROUND ART

It is known that ventricular tachycardia (VT) is common among patients with ventricular scar areas after a myocardial infarction. In this case, the electrical signal that passes through the ventricular myocardial affected area is inhomogeneously delayed, creating the ideal conditions for developing abnormal electrical circuits, electrical reentry loop type. Regardless of the etiology of the myocardial injury (myocardial ischemia—myocardial infarction sequelae, valvulopathy, sarcoidosis, congenital cardiac disease, arrhythmogenic ventricular dysplasia) [1], the substrate is represented by an inhomogeneous myocardial scar, composed of areas of fibrosis, an obstacle to electrical impulse transmission, and areas of viable myocardium, capable of conducting the electrical impulse slowly, the ideal support for intraventricular reentry [2, 3]. This may lead to an abnormal cardiac rhythm—TV type, or a completely chaotic rhythm—ventricular fibrillation type, a condition which may endanger the patient's life by the fact that the heart is not able to perform its primary function, that is, to pump blood. To eliminate areas of slow electrical conduction, within scar tissue, which are marked by abnormal electrical potential at ventricular level, the ablation method is especially used, and much more rarely, surgical excision of the affected tissue.

Figure 1:
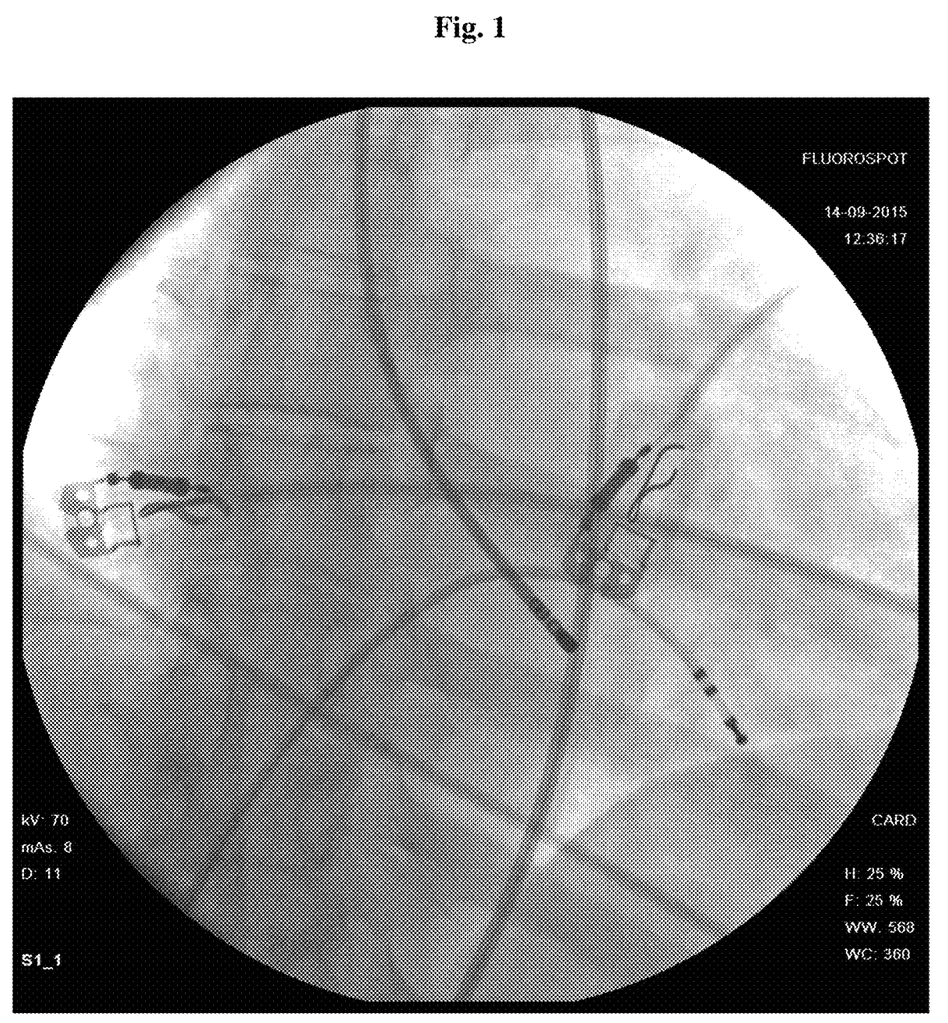
FIG. 1. Prior art: cartography of the left ventricle by conventional techniques—fluoroscopic guidance. The materials introduced into the heart are radioscopically visualized in order to be placed in various regions of the ventricular myocardium.

Radiofrequency ablation (RFA) of ventricular tachycardia (VT) is probably the most complex interventional procedure pertaining to cardiology, and represents a great challenge. The objective of RFA is to interrupt the reentrant circuit in its critical slow conducting area [4, 5]. Radiofrequency ablation consists of creating cauterization type point-like lesions in the critical area of the reentrant circuit. These lesions are made by the tip of an ablation catheter introduced in the heart (FIG. 1), in contact with the area detected as abnormal, the catheter being connected to a radiofrequency current generator with a medium-low frequency of 500 kHz. The lesion is obtained by heating the myocardium to a temperature of a minimum of 50 degrees, sufficiently large to cause irreversible lesion, and is based on the principle of coagulation necrosis.

The elimination of VT has evolved from conventional techniques of bidimensional cartography, in which the mapping of VT could be carried out exclusively during the tachycardia, based on cardiac stimulation maneuvers, the objective being to identify the exit point of the electrical impulse from the reentrant circuit (pacemapping technique), or the slow conduction area of the electrical impulse (entrainment technique), using radioscopic orientation, to modern mapping techniques which permit the identification and the elimination of the arrhythmogenic substrate (the area of low amplitude electrical potential and the presence of abnormal electrograms) outside of the tachycardia, in a stable sinus rhythm, using non-fluoroscopic mapping systems [6]. Even modern mapping techniques have the disadvantage of the imperfect localization of the scar area, and require long cartography times.

Performing an MRI for identifying the zonal and intramural extension of the fibrosis would be of great help in identifying the scar area before the RFA procedure. The disadvantage is that most patients with a structural cardiac disease, needing ablation of VT, already possess an implantable defibrillator (DEF), which makes impossible to perform the cardiac MRI before the ablation procedure. For this reason, the operator has no clues as to the extension of the myocardial fibrosis, and the electrocardiographic and echocardiographic localization offers only approximate criteria.

Figure 2:
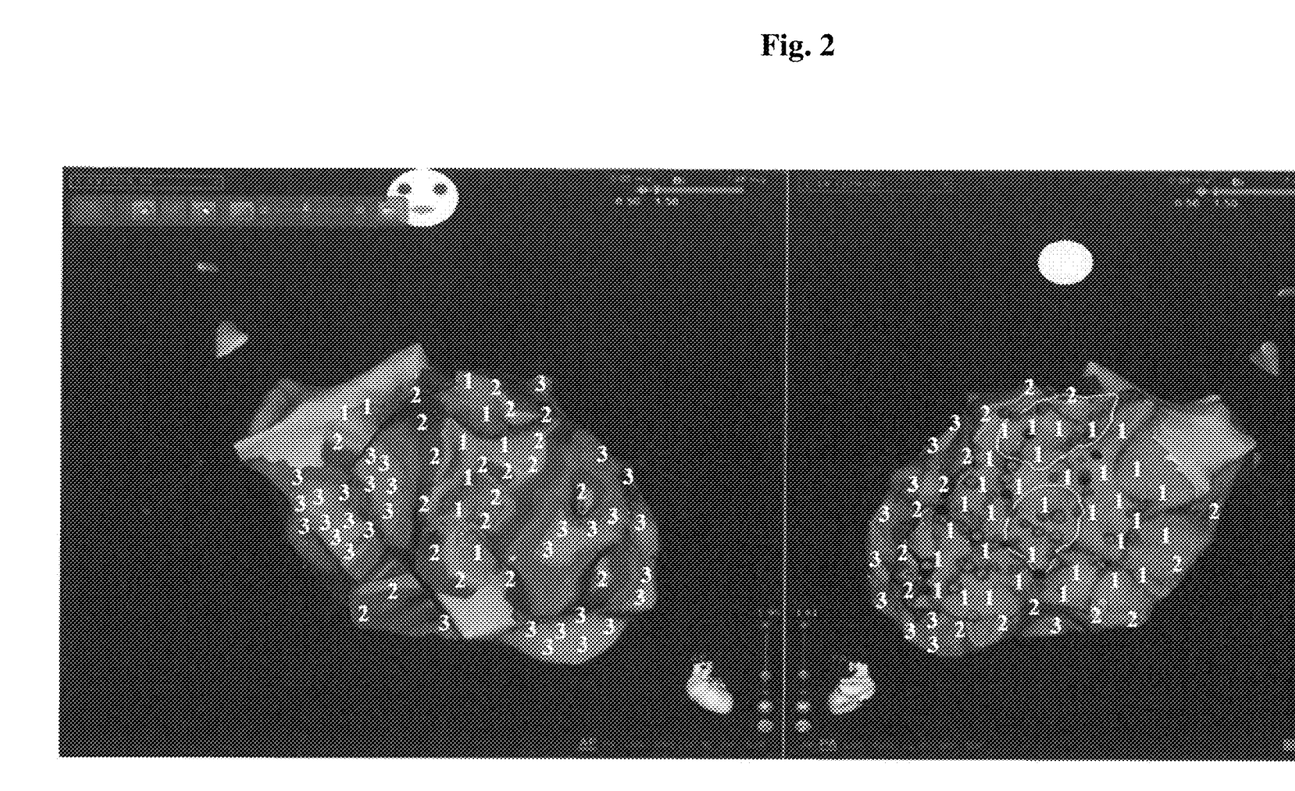
FIG. 2. Tridimensional cartography of the left ventricle (LV) in a patient with previous inferior myocardial infarction. The visualization of the catheter is done in a magnetic field which permits the construction of the LV's voltage map. 3A LV normal anterior wall 4B LF posterior scar wall. LV cartography in sinus rhythm automatically identifies the LV scar area in red (≤0.5 mV), the borderline region in green-blue (0.5-1.5 mV) and the normal myocardium in purple (≥1.5 mV). The marked points are manually annotated by the operator after analysis of shape, duration and amplitude of detected potential. Blue points manually marked represent pathological potentials, with high duration, low amplitude. Red points marked manually represent points of RF application.
Figure 3:
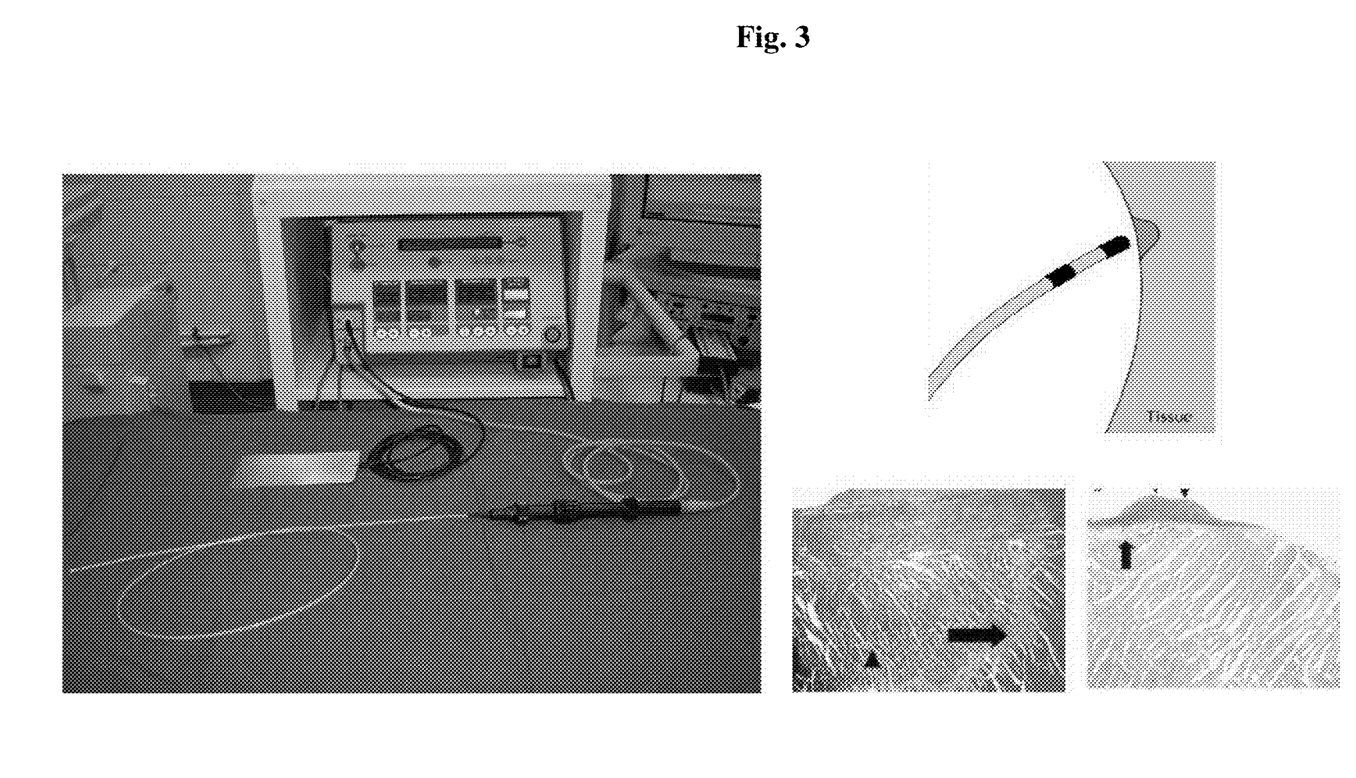
FIG. 3. Radiofrequency circuit which contains a RF generator connected to the catheter introduced into the patient, which has the metallic indifferent electrode applied to the posterior thorax. The mapping catheter during contact with the endocardium creates the radiofrequency lesion, which is small, well rounded, 1-2 mm, a consequence of coagulation necrosis.
Figure 4:
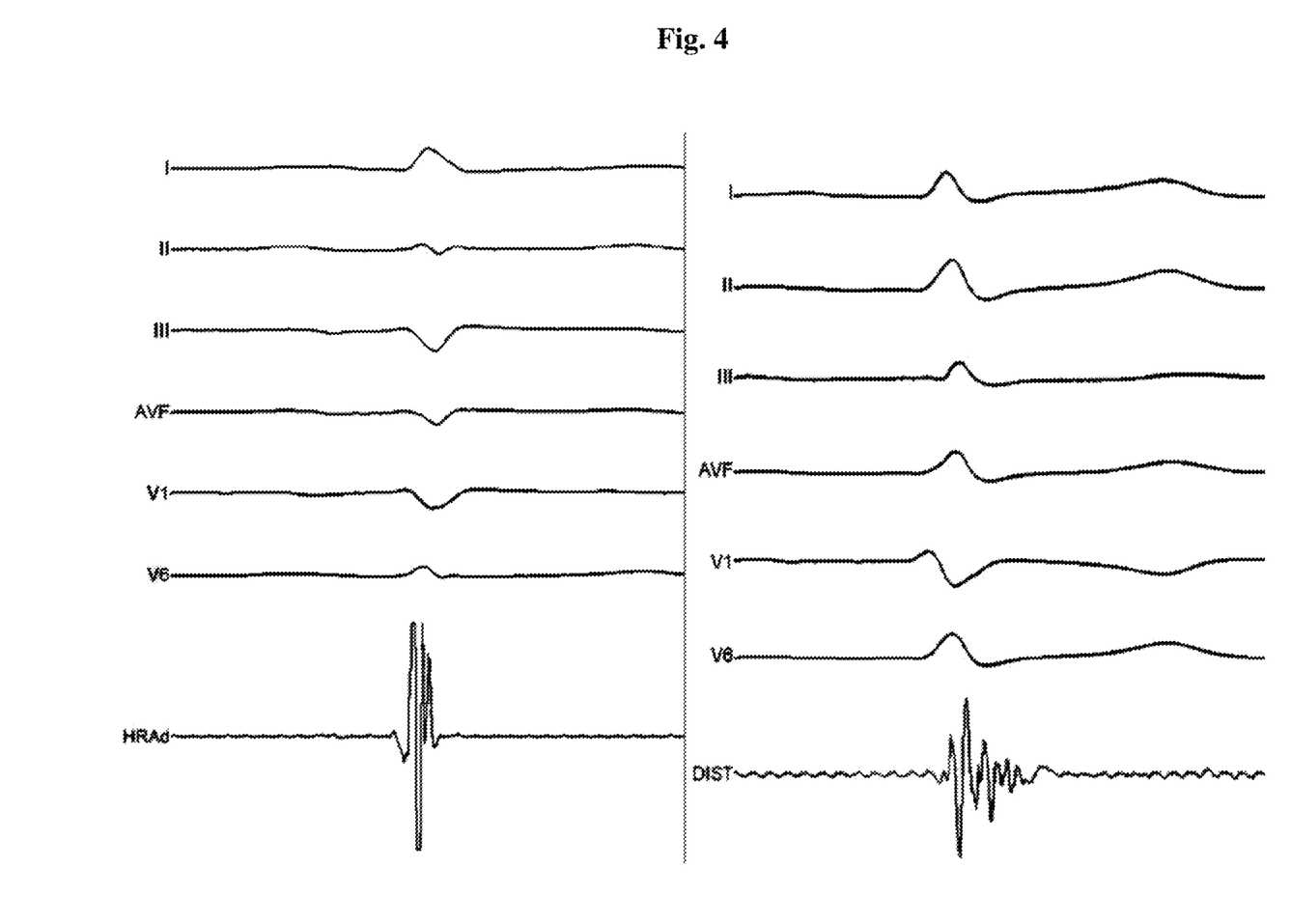
FIG. 4. I, II, III, AVF, V1, V6: surface electrocardiogram leads. Recording speed 300 mm/sec, 30-250 Hz filter. HRAd, DIST electrical potential detected by the distal electrode of mapping catheter. 4A Normal electrical potential with amplitude of over 1.5 mV, detected at start of QRS complex, in the first 50 ms. 4B Abnormal electrical potential, fragmented, with high frequency and duration, detected in last 40 ms of QRS complex and after the end of QRS complex.

The ablation of myocardial substrate, using the tridimensional mapping technique allows the elimination of non-inducible VT, or with hemodynamic degradation, by analyzing the arrythmogenic substrate, in stable sinus rhythm. Currently, the myocardium scar areas, borderline and normal, are identified by constructing the voltage map of the right or left ventricle using 3D cartography systems, the most widely used being CARTO 3D [7]. Conventionally, the myocardium scar area with microvolt potentials smaller than 0.5-1.5 mV is represented in red, the borderline area is represented in yellow-green, and the myocardium with normal amplitude electrical potential is represented in purple (FIG. 2).

The technique has multiple disadvantages: it requires the construction of a point by point map, it takes a long time, and the insufficient contact of the catheter with the myocardial wall may detect microvolt potentials which could be erroneously interpreted as fibrotic areas [8, 9], and for this reason there is a great concern among the interventional arrhythmologists to improve the method.

Interpreting abnormal electric potentials in the scar area is the most difficult, due to the lack of, at present, standardization elements. The analysis of electric potentials takes a long time, is approximate, is based greatly on the experience of the operator, and there are no reproducible criteria to ensure large-scale applicability of this technique. Being the only actual viable treatment alternative, efforts of the medical world are concentrated on the analysis of the electrical signal. Methods for determining the abnormal electrical signal points from the ventricular level are known, based on the amplitude of the received signal from the interior surface of the heart (endocardium). The disadvantage of this method is that the healthy points in the ventricle areas could be confounded with abnormal electrical potential areas, of risk in TV or ventricular arrhythmia, therefore being subjected to ablation. Also, some points of latent abnormal electrical potential may be omitted in the ablation process, which increases the rate of long term reoccurrence of tachycardia.

Other authors analyze the duration of the electrical potential. The greater the duration of the electrical potential in an area, the most it signifies that the electrical potential is being slowly transmitted in that area, and abnormal electric loops may occur, having the clinical manifestation of VT. Identifying the abnormal electrical potentials in normal cardiac rhythm opens the perspective of treating those ventricular tachycardias which are not hemodinamically tolerated, during which arterial blood pressure drops, the patient loses consciousness, and the origin of the tachycardia cannot be identified. On the other hand, treating a single ventricular tachycardia does not lower the patient's arrhythmic risk, as most patients develop several morphologies of ventricular tachycardia, that is why it is important to treat the entire scar area.

More than 50% of patients who have an RFA VT procedure by conventional 2D means have the reoccurrence of the arrhythmia in the following years, post-procedure. Using 3D means of targeted and thorough cartography of the scar area has improved RFA results in the past few years, with the possibility of obtaining encouraging long-term results, 80% of patients being without arrhythmic events 2 years after the procedure [10, 11]. For this reason, in more and more centers around the world, the treatment of VT is done by 3D means, despite the costs being much greater compared to the 2D technique.

Conventionally, the ablation catheter is placed within the heart, using radioscopy for visualization. Existing means and techniques for tridimensional cartography (mapping) used in cardiac ablation allow for the creation of a virtual image of the heart cavity, using the magnetic field. Thus, the catheter may be precisely placed in a certain area, the abnormal point may be marked on the virtual map, prior ablated points may be marked as well, and it is possible to come back upon the points marked as abnormal at the moment of ablation after the overall analysis has been performed.

Current 3D cartography systems automatically define the abnormal scar area based only on the amplitude of electric potential, on the basis of which a voltage map is constructed. Afterwards, the physician does a thorough analysis, point by point, of the area grossly detected as scar, and defines the electrical potentials as being abnormal by manual measurement, using also other criteria than the ones related to the electrical signal amplitude.

Technical Problem

The technical problem consists of accurately determining, on the interior surface of the ventricular myocardium, the points with an abnormal electrical potential, in a short interval of time.

The proposed solution consists of an apparatus which digitally interprets the acquired signals and automatically warns acoustically and/or by warning light, pointing out the electrical potential which meets the abnormal electrical potential criteria.

The decision of treating that specific point by applying the radiofrequency current remains in the hands of the physician, who may also perform, at the same time, a classical, manual interpretation of the signal.

BRIEF DESCRIPTION OF THE INVENTION

The apparatus for determining abnormal electrical potential points found in the ventricular myocardium contains an amplification and analogue filtration module, an analogue to digital signal convertor, a hardware device which contains a microchip for the digital processing, via software, of the signals received from an EKG and from a catheter, a display for visualizing the signals received from the EKG, and from the catheter, as well as the abnormal electrical potentials coming from the ventricular myocardium, identified by means of the software. The software analyzes the signal coming from catheter referring to the amplitude, duration and synchronization with the QRS complex of the signal coming from the EKG, as well as the spectral fragmentation degree (FFT analysis). The software activates the exclusion condition of eventual artifact signals, the signal being considered normal and the other search intervals being automatically ignored if the level of the signal coming from the catheter is over the established voltage threshold (preferably 1.5 mV), in a search interval up to 50 ms after the start of the QRS complex, that is, the Q point. Also, the software activates the condition for detecting an abnormal signal if the level of the signal coming from the catheter has an amplitude over the second established threshold (preferably under 0.5 mV) and is situated in a search interval of 50 ms before and up to 100 ms after the end of the QRS complex, that is, the S point. The levels of the voltage thresholds and search intervals may be adjusted on a case by case basis.

Optionally, the apparatus may contain a device to produce an acoustic or luminous signal when the catheter touches a point of abnormal potential on the surface of the heart.

In a first example, the apparatus may be coupled with an EKG and a catheter.

In a second example, the apparatus may contain an EKG and have a connection for a catheter.

The apparatus is used in the ablation procedure of the ventricular myocardium, the points of abnormal electrical potential which are detected by the apparatus being able to be ablated as soon as they are detected, or later.

The apparatus may be utilized with a 2D or 3D cardiac mapping system, or with any system that permits the cartography and highlighting of the used signals.

Advantages

The invention has multiple advantages:
increases the accuracy for determining points of abnormal electrical potential;
shortens the cartography time (currently, the procedure takes approx. 4-5 h, on average);
minimizes the number of radiofrequency application points to the area of the reentrant circuit and therefore may diminish risk of myocardial perforation and coronary occlusion when the application of radiofrequency is to the epicardial region [12];
eases the physician labor;
lessens the exposure time to radiation, particularly for conventional mapping systems;
impossibility of inducing ventricular arrhythmia after RFA treatment of the entire scarred area;
saving healthy tissue adjacent to affected areas by reduction of false ablation points;
offers physician coherent feedback in decision to validate electrical potential, therefore may decrease the number of operating physicians.

BRIEF DESCRIPTION OF THE DRAWINGS

The following two embodiments of the invention are given in connection with the figures representing.

DESCRIPTION OF THE EMBODIMENTS

Apparatus (1) for determining the abnormal electrical potential points occurring in the ventricular myocardium, according to invention, comprises:
- a module (2) for amplification and analogue filtering of the signal from an EKG device (3) and from a catheter (4). The amplifier has the role of amplifying the input voltage up to a value which allows the signal detection and digitization. The level of amplification is selectable, or may be automatically achieved within the interval between 10× and 1000×. The analogue filter has the role of retaining from the received signal (EKG and catheter) only the frequencies of interest and removing the noise caused by the connection cables especially. The band pass filters are utilized with a range that is selectable from an interval of 0.01 Hz-500 Hz, and notch filter with a frequency of 50 Hz and/or 60 Hz for removing the noise due to the electrical network. For the signals coming from the catheter, one or more amplifications and filtration channels may be used;
- an analogue to digital signal converter (5) which converts the amplified analogue signals into sequences of numbers which may then be digitally processed. The sampling rate of the signal is chosen depending on the frequency range of interest, having to be at least two times greater than the maximum value of the frequency. For a correct reproduction of the signals in the frequency range of interest, sampling rate of 5000 samples/second is recommended (5 kS/s);
- a hardware device (6), such as a computer, microcontroller or any other equivalent device, for digital data processing. The digital signal processor has the role of running a software (7) which is based on the algorithm presented in FIG. 8, for real time processing and analyses of the EKG and catheter signals.
- a display (8) for visualization of the signals received from the EKG and the catheter, and also the obtained results;
- optionally, a device (9) for generating an acoustic or luminous signal when the catheter reaches a point with abnormal intracardiac electric potential.

In a first embodiment, the apparatus according to the invention, is conceived to be connected to the EKG device (3) and to the catheter (4) through known means. The EKG device (3) is necessary to produce the EKG deviations of interest utilizing signals coming from the surface electrodes placed on the patient. Recording the surface electrocardiogram is used for QRS complex detection, representing the main deflection of the EKG signal corresponding to ventricular depolarization—the electrical expression of the contraction of the heart pumps. For the detection of the QRS complex, at least one EKG deviation is used.

Figure 5:
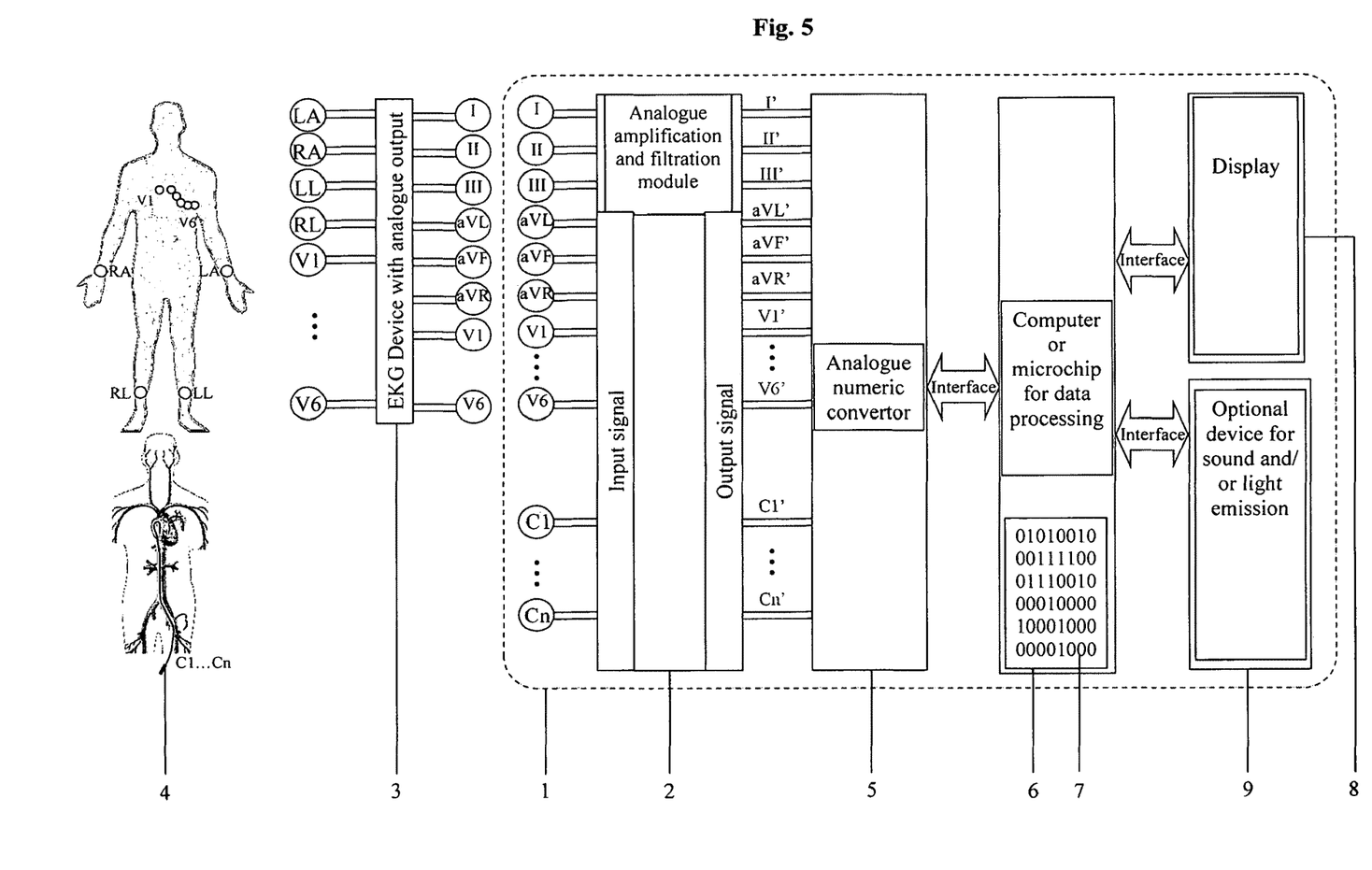
FIG. 5. Block diagram of apparatus for detection of abnormal potentials with EKG signals supplied by external analogue EKG machine.
Figure 6:
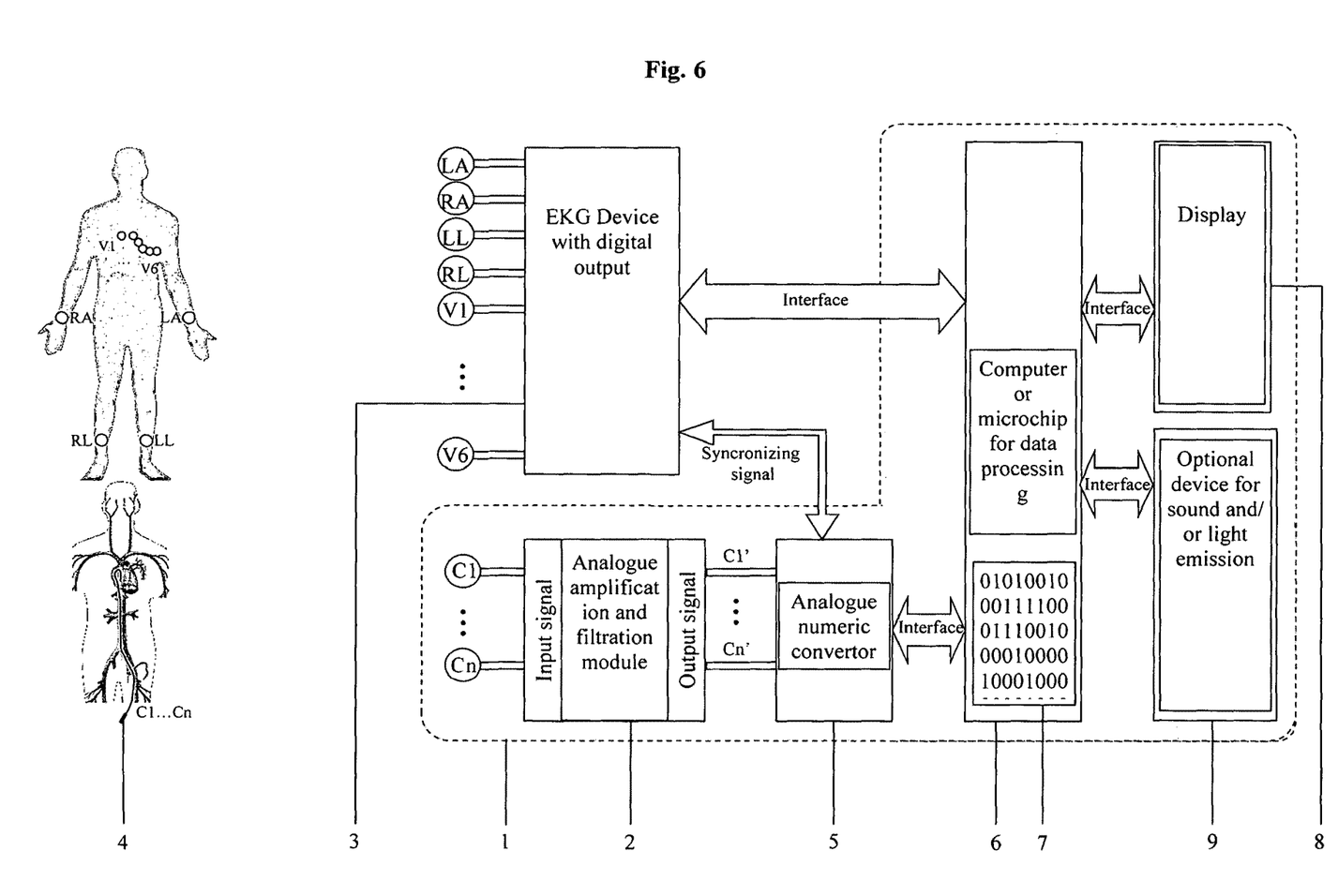
FIG. 6. Block diagram of apparatus for detection of abnormal potentials with EKG signals supplied by external digital EKG machine.

The EKG device (3) may be analogue, according to the block diagram of FIG. 5, or digital, according to the block diagram of FIG. 6.

Figure 7:
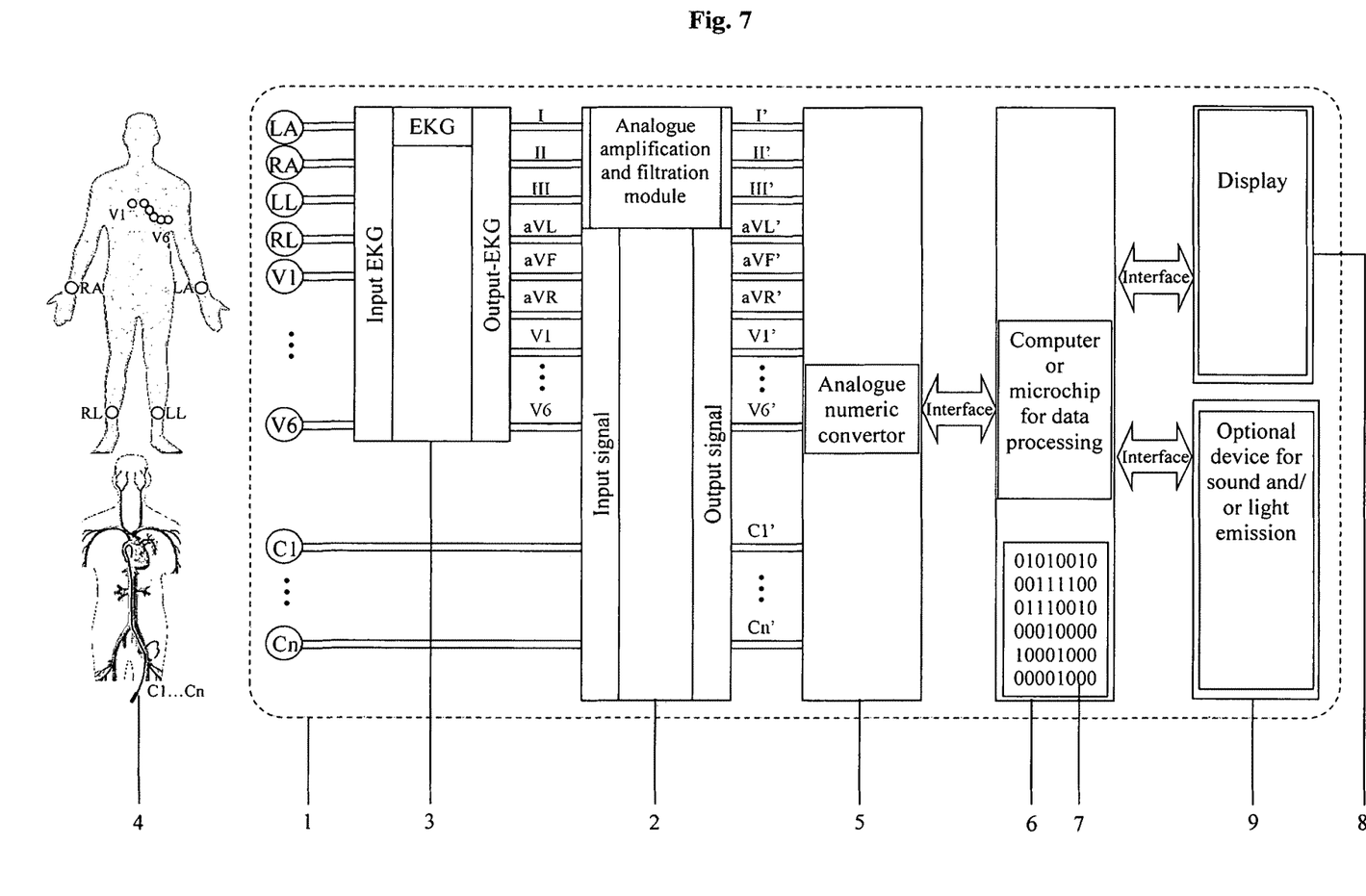
FIG. 7. Block diagram of device for detection of abnormal potentials with built-in EKG machine.

In a second embodiment, the apparatus according to the invention, contains the EKG signal measuring device (3) built-in, according to block diagram from FIG. 7. In this case, as well, the apparatus contains the means to connect to the catheter (4).

Figure 8:
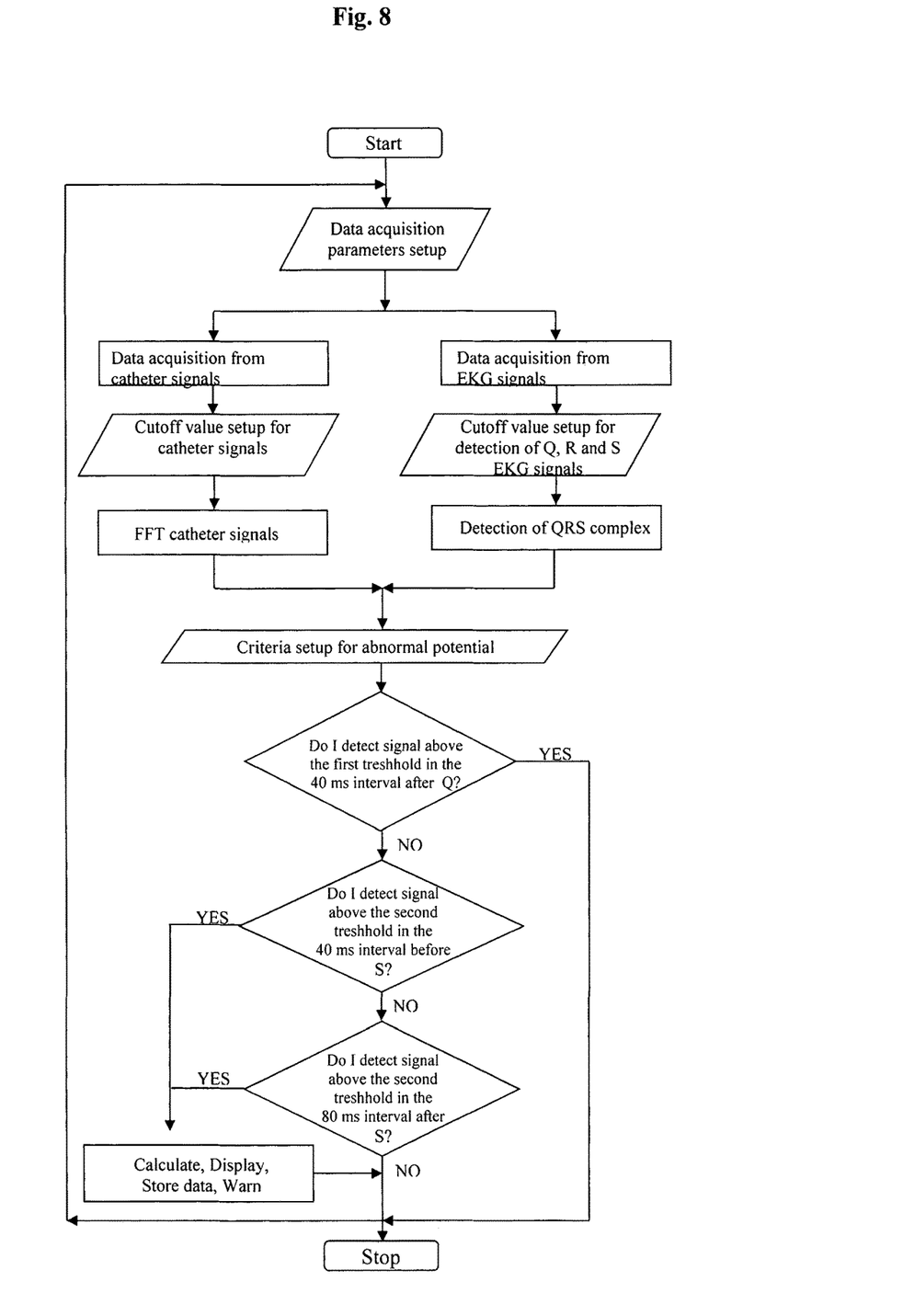
FIG. 8. Logic diagram of algorithm for detection of abnormal intracardiac signals.

The apparatus, according to the invention, integrates an algorithm to detect abnormal intracardiac signals, algorithms which are based on a set of criteria to differentiate between normal and abnormal signals. These differentiation and real time selection criteria consider the following characteristics of the signal coming from the catheter:
- amplitude;
- duration;
- QRS synchronization of the signal received by the EKG surface electrodes;
- fragmentation (spectral composition).

Typically, the catheter signal corresponding to an area of normal cardiac tissue, has an amplitude greater than 1.5 mV, a well-defined duration (is not fragmented, that is, it has an aspect of a biphasic signal, with 1-2 components, and a duration smaller than the QRS complex) and is synchronized to the signal received by the surface electrodes, that is the QRS complex of the EKG signal. The implemented detection algorithm considers all these characteristics, establishes certain search intervals and introduces certain exclusion conditions. The apparatus allows the acquisition (analogue digital conversion) with a sampling rate of 5 kS/s of the two relevant signals, the EKG surface signal and the intracardiac signal from the catheter. The algorithm analyzes the EKG signal and detects the specific QRS complex. In the case of the signal coming from the catheter, a spectral (FFT) analysis is performed, to evaluate the degree of fragmentation. In the established search intervals, the synchronization of the two signals is analyzed, as follows:

in the search interval up to 50 ms after the beginning of the QRS complex, preferably 40 ms after the beginning of the QRS complex, that is the Q point, the level of the signal originating in the catheter is verified, and if a signal is found over the first established threshold (preferably 1.5 mV) the exclusion criteria for possible artifact signals is activated, in such a way that the signal is considered to be normal, the other search intervals being automatically ignored;

in the search interval up to 50 ms after the beginning of the QRS complex, preferably 40 ms after the beginning of the QRS complex, that is the S point, the level of the catheter signal is verified, and if the second established threshold is exceeded (preferably under 0.5 mV), the abnormal signal detection condition is activated;

in the search interval up to 100 ms after the end of the QRS complex, preferably 80 ms after the end of the QRS complex, that is the S point, the level of the catheter signal is verified, and if the second established threshold is exceeded, the abnormal signal detection condition is activated.

The reference for the search intervals of the potential abnormal signals is adjustable, and particular to each case.

When the abnormal intracardiac signal detection condition is activated, the characteristics of the abnormal intracardiac signal are calculated, displayed and memorized: amplitude of signal, duration of signal, degree of desynchronization (position of maximum point in relation to the end of the QRS complex, that is the S point). The acoustic and/or luminous warning is automatically activated for the intracardiac abnormal signal, for marking the detected area as an ablation point.

The apparatus, according to invention, may be used with any mapping system, 2D or 3D, at a cardiac level, as well as any other system that allows cartography and highlighting the used signals, in any system, to perfect determination of abnormal electrical potentials at a myocardial level.

In case of utilizing a 2D mapping system, the ablation of areas with abnormal electrical potential is done instantly.

In case of utilizing a non-invasive 3D mapping system, the areas with abnormal electrical potential from the myocardium may be identified prior to the ablation procedure.

Thus, the apparatus, according to the invention, may be attached to the conventional mapping catheter, which is fluoroscopically visualized, as well as to the tridimensional electroanatomical cartography catheter, both used in procedures of cardiac ablation, because they automatically analyze and interpret electrical potential only, independent of the ablation catheter localization means within the heart.

A very good consistency has been found between the automatic identification of abnormal electrical potential points from the ventricular myocardium with the aid of the apparatus, according to the invention and the effect of the intervention on patients for which ventricular ablation was performed.

Considering that during a procedure, the electrical signals from approximately 200-400 points are analyzed, it is absolutely necessary to sort and define them by the software according to the invention, which has the technical effect of increasing the speed of determination of the ablation points, as well as increasing the accuracy for determining said points, which significantly shortens the procedure time for a ventricular ablation and increases the success rate thereof.

BIBLIOGRAPHY

[1] Raymond J.-M., Sacher F., Winslow R., Tedrow U., et al. *Catheter ablation for scar-related ventricular tachycardias*. Curr Probl Cardiol, 2009, 34, p. 225-270.

[2] de Bakker J. M., van Capelle F. J., Janse M. J., et al. *Reentry as a cause of ventricular tachycardia in patients with chronic ischemic heart disease: Electrophysiologic and anatomic correlation*. Circulation, 1988, 77, p. 589-606.

[3] Haqqani H. M., Marchlinski F. E. *Electrophysiologic substrate underlying postinfarction ventricular tachycardia: characterization and role in catheter ablation*. Heart Rhythm, 2009, 6, p. S70-S76.

[4] Desjardins B., Crawford T., Good E., et al. *Infarct architecture and characteristics on delayed enhanced magnetic resonance imaging and electroanatomic mapping in patients with postinfarction ventricular arrhythmia*. Heart Rhythm, 2009, 6(5) p. 644-651.

[5] Wissner E., Stevenson W. G., Kuck K. H. *Catheter ablation of ventricular tachycardia in ischaemic and non-ischaemic cardiomyopathy: where are we today? A clinical review*. European Heart Journal, 2012, 33, p. 1440-1450.

[6] Stevenson W. G., Khan H., Sager P., et al. *Identification of reentry circuit sites during catheter mapping and radiofrequency ablation of ventricular tachycardia late after myocardial infarction*. Circulation, 1993, 88, p. 1647-1670.

[7] Arenal A., del Castillo S., Gonzalez-Torrecilla E., et al. *Tachycardia-related channel in the scar tissue in patients with sustained monomorphic ventricular tachycardias: Influence of the voltage scar definition*. Circulation. 2004, 110, p. 2568-2574.

[8] Aliot E. M., Stevenson W. G., Almendral-Garrote J. M., et al. *EHRA/HRS expert consensus on catheter ablation of ventricular arrhythmias*. Heart Rhythm, 2009, 6(6), p. 886-933.

[9] Wijnmaalen A. P., van der Geest R. J., van Huls van Taxis C. F., et al. *Head-to-head comparison of contrast-enhanced magnetic resonance imaging and electroanatomical voltage mapping to assess post-infarct scar characteristics in patients with ventricular tachycardias: real-time image integration and reversed registration*. Eur Heart J, 2011, 32 p. 104-14.

[10] Vergara P., Trevisi N., Ricco A., et al. *Late potentials abolition as an additional technique for reduction of arrhythmia recurrence in scar related ventricular tachycardia ablation*. J Cardiovasc Electrophysiol, 2012, 23, p. 621-627.

[11] Berruezo A., Fernández-Armenta J., Andreu D., et al. *Scar Dechanneling: A New Method for Scar-Related Left Ventricular Tachycardia Substrate Ablation*. Circ Arrhythm Electrophysiol. published online Jan. 12, 2015; DOI: 10.1161/CIRCEP.114.002386.

[12] Fernández-Armenta J., Berruezo A., Ortiz-Perez J. T., et al. *Improving Safety of Epicardial Ventricular Tachycardia Ablation Using the Scar Dechanneling Technique and the Integration of Anatomy, Scar Components, and Coronary Arteries Into the Navigation System*. Circulation, 2012, 125, p. e466-e468.

The invention claimed is:

1. An apparatus for determining abnormal electrical potential points from a ventricular myocardium that require ablation, comprising:
   a module for amplification and analogue filtering,
   an analogue-digital signal converter, a hardware device for digital real time processing of data, by a software, of signals received from an EKG device and from a catheter, the abnormal electrical potentials from the ventricular myocardium being identified by the software, assisting in preserving viable ventricular myocardium, the software analyzing the signal received from the catheter, respectively amplitude, duration, synchronization with a QRS complex of the signal coming from EKG surface electrodes, as well as spectral fragmentation (FFT analysis) to establish search intervals and exclusion conditions, and activating an exclusion condition for eventual artifact signals, a signal from the catheter being considered normal and other search intervals being automatically ignored if a level of the catheter signal exceeds a first voltage threshold that was established, in a search interval of up to 50 ms after the beginning of the QRS complex, the Q point respectively, and by that it activates a condition for detection of the abnormal signal, if the level of the catheter signal has an amplitude over a second voltage threshold that was established, and is situated in a search interval of up to 50 ms before and up to 100 ms after the end of the QRS complex, the S point respectively; and a display for displaying the signals received from the EKG device and from the catheter, and the abnormal electrical potentials from the ventricular myocardium.

2. The apparatus according to claim 1, further comprising a device for generating one of, an acoustic, or luminous visual signal when the catheter reaches an abnormal electrical potential from the ventricular myocardium.

3. The apparatus according to claim 1, wherein said apparatus is configured to connect to an EKG device and a catheter.

4. The apparatus according to claim 1, comprising a built-in EKG device and a connection for a catheter.

5. The apparatus according to claim 1, wherein a reference for the search intervals for abnormal signals is adjustable and is singularized for each case.

6. The apparatus according to claim 1, the abnormal electrical potential points detected by the apparatus being configured to be simultaneously or latterly ablated.

7. The apparatus according to claim 1, further comprising a 2D or 3D mapping system, on cardiac level, or with any system that allows the cartography and highlighting of the used signals.

8. The apparatus according to claim 2, wherein said apparatus is connectable to an EKG device and a catheter.

9. The apparatus according to claim 2, comprising a built-in EKG device and a connection for a catheter.

10. The apparatus according to claim 2, the abnormal electrical potential points detected by the apparatus being configured to be simultaneously or latterly ablated.

11. The apparatus according to claim 3, the abnormal electrical potential points detected by the apparatus being configured to be simultaneously or latterly ablated.

12. The apparatus according to claim 8, the abnormal electrical potential points detected by the apparatus being configured to be simultaneously or latterly ablated.

13. The apparatus according to claim 4, the abnormal electrical potential points detected by the apparatus being configured to be simultaneously or latterly ablated.

14. The apparatus according to claim 9, the abnormal electrical potential points detected by the apparatus being configured to be simultaneously or latterly ablated.

15. The apparatus according to claim 5, the abnormal electrical potential points detected by the apparatus being configured to be simultaneously or latterly ablated.

16. The apparatus according to claim 2, further comprising one of, a 2D or 3D mapping system, on cardiac level, or with any system that allows the cartography and highlighting of the used signals.

17. The apparatus according to claim 5, further comprising one of, a 2D or 3D mapping system, on cardiac level, or with any system that allows the cartography and highlighting of the used signals.

18. The apparatus according to claim 1, wherein the hardware device is a computer or a microcontroller.

\* \* \* \* \*

UNITED STATES PATENT AND TRADEMARK OFFICE
CERTIFICATE OF CORRECTION

| | |
|---|---|
| PATENT NO. | : 11,344,247 B2 |
| APPLICATION NO. | : 16/308191 |
| DATED | : May 31, 2022 |
| INVENTOR(S) | : Horia Chiriac et al. |

It is certified that error appears in the above-identified patent and that said Letters Patent is hereby corrected as shown below:

In the Specification (1) In Column 7, Line 14, please change "after" to --before--;

(2) In Column 7, Line 14, please change "beginning" to --end--;

(3) In Column 7, Line 15, please change "after" to --before--; and (4) In Column 7, Line 15, please change "beginning" to --end--.

Signed and Sealed this
Nineteenth Day of July, 2022

Katherine Kelly Vidal
*Director of the United States Patent and Trademark Office*